US012674798B2

(12) United States Patent
Hwang et al.

(10) Patent No.: US 12,674,798 B2
(45) Date of Patent: Jul. 7, 2026

(54) PATHOGEN DETECTION METHOD AND APPARATUS

(71) Applicants: UIF (University Industry Foundation), Yonsei University, Seoul (KR); Industry Academic Cooperation Foundation of Yeungnam University, Gyeongsangbuk-do (KR)

(72) Inventors: Jung Ho Hwang, Seoul (KR); Dae Hoon Park, Seoul (KR); Hyeong Rae Kim, Seoul (KR); Sang Gwon An, Gyeonggi-do (KR); Sung Jae Park, Seoul (KR); Jeong Hoon Byeon, Gyeongsangbuk-do (KR)

(73) Assignees: UIF (UNIVERSITY INDUSTRY FOUNDATION), YONSEI UNIVERSITY, Seoul (KR); INDUSTRY ACADEMIC COOPERATION FOUNDATION OF YEUNGNAM UNIVERSITY, Gyeongsangbuk-Do (KR)

( * ) Notice: Subject to any disclaimer, the term of this patent is extended or adjusted under 35 U.S.C. 154(b) by 1333 days.

(21) Appl. No.: 17/472,985

(22) Filed: Sep. 13, 2021

(65) Prior Publication Data

US 2022/0082555 A1 Mar. 17, 2022

(30) Foreign Application Priority Data

Sep. 14, 2020 (KR) ........................ 10-2020-0117559

(51) Int. Cl.
*G01N 33/533* (2006.01)
*B01J 31/00* (2006.01)
(Continued)

(52) U.S. Cl.
CPC .......... *G01N 33/533* (2013.01); *B01J 31/003* (2013.01); *C12N 9/0069* (2013.01);
(Continued)

(58) Field of Classification Search
CPC ............ G01N 33/533; G01N 33/54346; B01J 31/003; C12N 9/0069; B82Y 5/00; B82Y 35/00; B82Y 40/00; C12Y 113/12
See application file for complete search history.

(56) References Cited

U.S. PATENT DOCUMENTS 5,918,259 A * 6/1999 Squirrell .................. C12Q 1/24
356/438
6,319,668 B1* 11/2001 Nova ....................... C07K 1/04
435/7.1
(Continued)

FOREIGN PATENT DOCUMENTS

| KR | 1020170074730 A | 6/2017 |
| KR | 10-2019-0030146 A | 3/2019 |
| KR | 1020288210000 B1 | 9/2019 |

OTHER PUBLICATIONS

Hsiang-Yu Chang et al., "Synthesis and Antimicrobial Activity of Gold/Silver—Tellurium Nanostructures", 2014 American Chemical Society.

(Continued)

*Primary Examiner* — Brian R Gordon
(74) *Attorney, Agent, or Firm* — Tarolli, Sundheim, Covell & Tummino LLP

(57) ABSTRACT

A pathogen detection method includes forming nanoparticles, extracting adenosine triphosphate (ATP) by causing the nanoparticles to collide with pathogens, collecting the pathogens having collided with the nanoparticles, and detecting a light-emitting reaction formed by a reaction with the ATP.

6 Claims, 7 Drawing Sheets

(51) Int. Cl.

| | | |
|---|---|---|
| *C12N 9/02* | (2006.01) | |
| *G01N 33/543* | (2006.01) | |
| *B82Y 5/00* | (2011.01) | |
| *B82Y 35/00* | (2011.01) | |
| *B82Y 40/00* | (2011.01) | |

(52) U.S. Cl.

CPC .......... *G01N 33/54346* (2013.01); *B82Y 5/00*
(2013.01); *B82Y 35/00* (2013.01); *B82Y 40/00*
(2013.01); *C12Y 113/12* (2013.01)

(56) References Cited

U.S. PATENT DOCUMENTS

| | | | | |
|---|---|---|---|---|
| 6,340,588 | B1 * | 1/2002 | Nova ........................ | C07K 1/00 435/287.1 |
| 2005/0070025 | A1 * | 3/2005 | Mooradian ........ | G01N 15/0625 436/178 |
| 2007/0248957 | A1 * | 10/2007 | Nova ...................... | B82Y 10/00 435/7.1 |
| 2008/0176209 | A1 * | 7/2008 | Muller .................... | B01L 3/545 435/235.1 |
| 2009/0304803 | A1 * | 12/2009 | Hasan ................ | A61K 47/6935 424/497 |
| 2010/0062415 | A1 * | 3/2010 | Schwoebel ............ | G01N 21/07 435/5 |
| 2015/0099272 | A1 * | 4/2015 | Hwang .................... | C12Q 1/04 435/34 |
| 2016/0231324 | A1 * | 8/2016 | Zhao ................ | G01N 33/57496 |

OTHER PUBLICATIONS

Benjamin Hindson, et al.; "APDS: The Autonomous Pathogen Detection System"; Biosensors and Bioelectronics; Lawrence Livermore National Laboratory UCRL-JRNL-207074; Oct. 6, 2004; 23 pgs.

* cited by examiner

PATHOGEN DETECTION METHOD AND APPARATUS

CROSS-REFERENCE TO RELATED APPLICATION

This application claims priority to and the benefit of Korean Patent Application No. 10-2020-0117559, filed on Sep. 14, 2020, the disclosure of which is incorporated herein by reference in its entirety.

BACKGROUND

1. Field of the Invention

The present invention relates to a pathogen detection method and apparatus.

2. Discussion of Related Art

A technique that detects pathogens (viruses, bacteria, or the like) in air is essential in a management of infection through air. A technique that detects pathogens includes a process of collecting pathogens in air, and a process of obtaining information on pathogens by measuring collected particles.

In the related art, in a technique that measures pathogens in air, there is a problem that a duration of a signal formed by detecting pathogens is short, and thus, it is difficult to detect the pathogens. There are several techniques for addressing this shortcoming, but even in the several techniques, there is also a disadvantage in that a measurer should perform a manual operation for each measurement and a cost of a detection device increases since an additional factor is used.

SUMMARY OF THE INVENTION

The present invention is directed to a pathogen detection method and apparatus capable of more easily measuring pathogens in air and further decreasing costs compared to the related art.

According to an aspect of the present invention, there is provided a pathogen detection method including forming nanoparticles, extracting adenosine triphosphate (ATP) by causing the nanoparticles to collide with pathogens, collecting the pathogens having collided with the nanoparticles, and detecting a light-emitting reaction formed by a reaction with the ATP.

According to another aspect of the present invention, there is provided a pathogen detection apparatus including a nanoparticle forming chamber in which nanoparticles are formed, an impact unit configured to cause the nanoparticles to collide with the pathogens so that ATP is extracted from the pathogens, and a detector including a collector provided with the pathogens having collided with the nanoparticles to collect the pathogens having collided with the nanoparticles and a sensor configured to detect a light-emitting reaction formed by a reaction with the ATP collected by the collector.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION OF EXEMPLARY EMBODIMENTS

Figure 1:
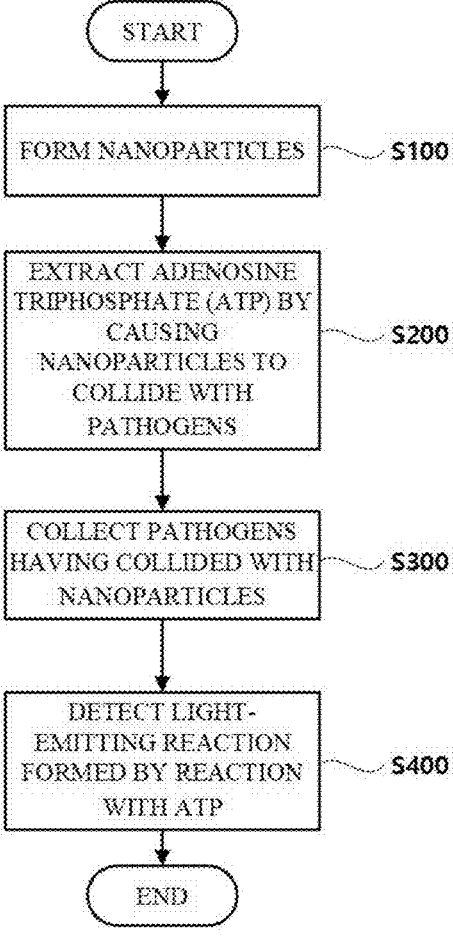
FIG. 1 is a flowchart illustrating an overview of a pathogen detection method according to one exemplary embodiment of the present invention.
Figure 2:
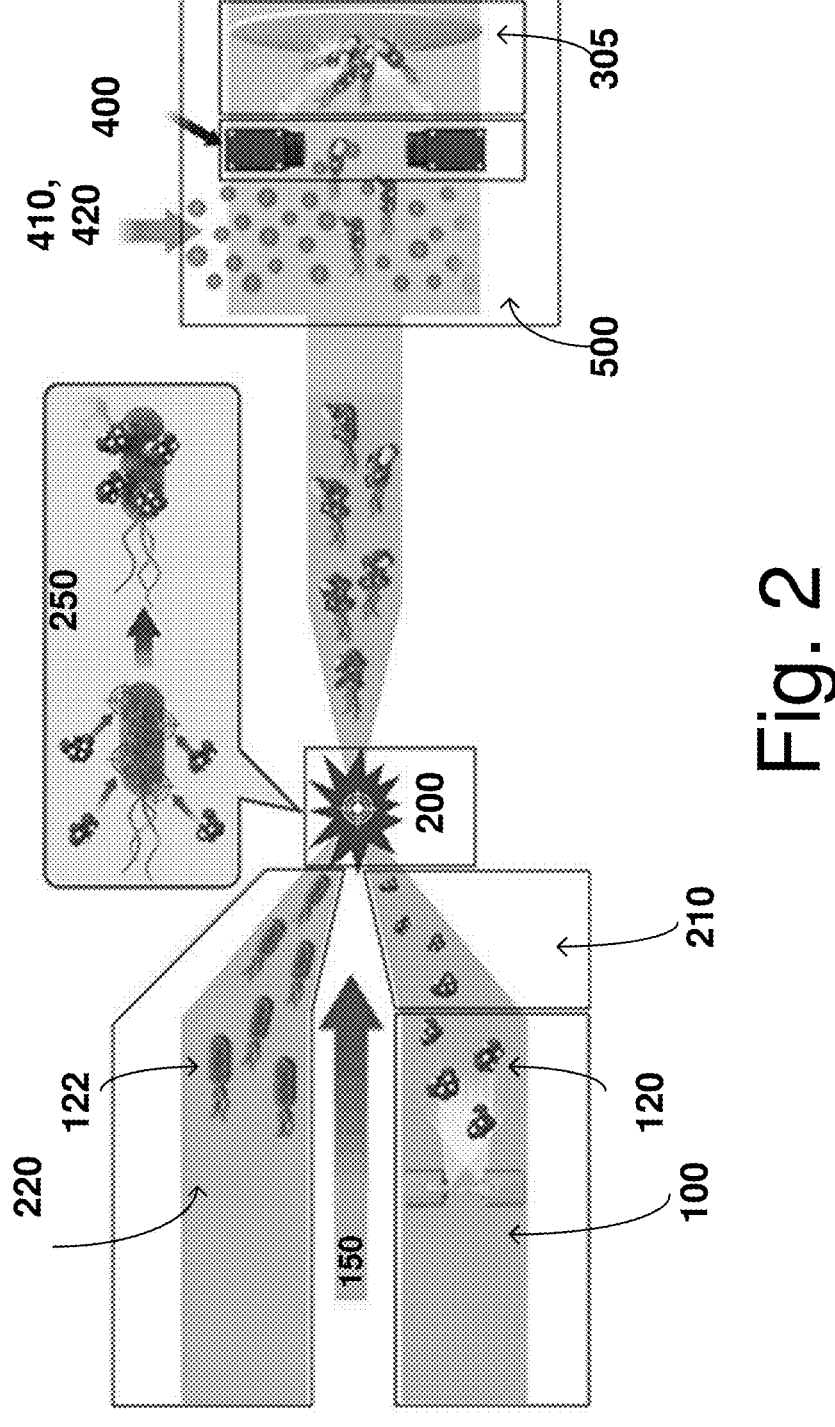
FIG. 2 is a schematic diagram illustrating an overview of the pathogen detection method and a pathogen detection apparatus according to one exemplary embodiment of the present invention.

Hereinafter, a pathogen detection method and a pathogen detection apparatus according to exemplary embodiments of the present invention will be described with reference to the accompanying drawings. FIG. 1 is a flowchart illustrating an overview of a pathogen detection method according to one exemplary embodiment of the present invention and FIG. 2 is a schematic diagram illustrating an overview of the pathogen detection method and a pathogen detection apparatus according to one exemplary embodiment of the present invention. Referring to FIG. 1, the pathogen detection method according to the present embodiment includes a step S100 of forming nanoparticles 120, a step S200 of extracting adenosine triphosphate (ATP) by causing the nanoparticles 120 to collide with pathogens 122, a step S300 of collecting the pathogens 122 to which the nanoparticles 120 are attached, and a step S400 of detecting a light-emitting reaction formed by a reaction with the ATP.

FIG. 2 shows a schematic illustration of the pathogen detection apparatus including a nanoparticle forming chamber 100 in which nanoparticles 120 are formed, an impact unit 200 where nanoparticles 120 collide with pathogens 122 at an impact point 250, and a detector 500 including a collector 305 and a sensor 400.

Figure 3:
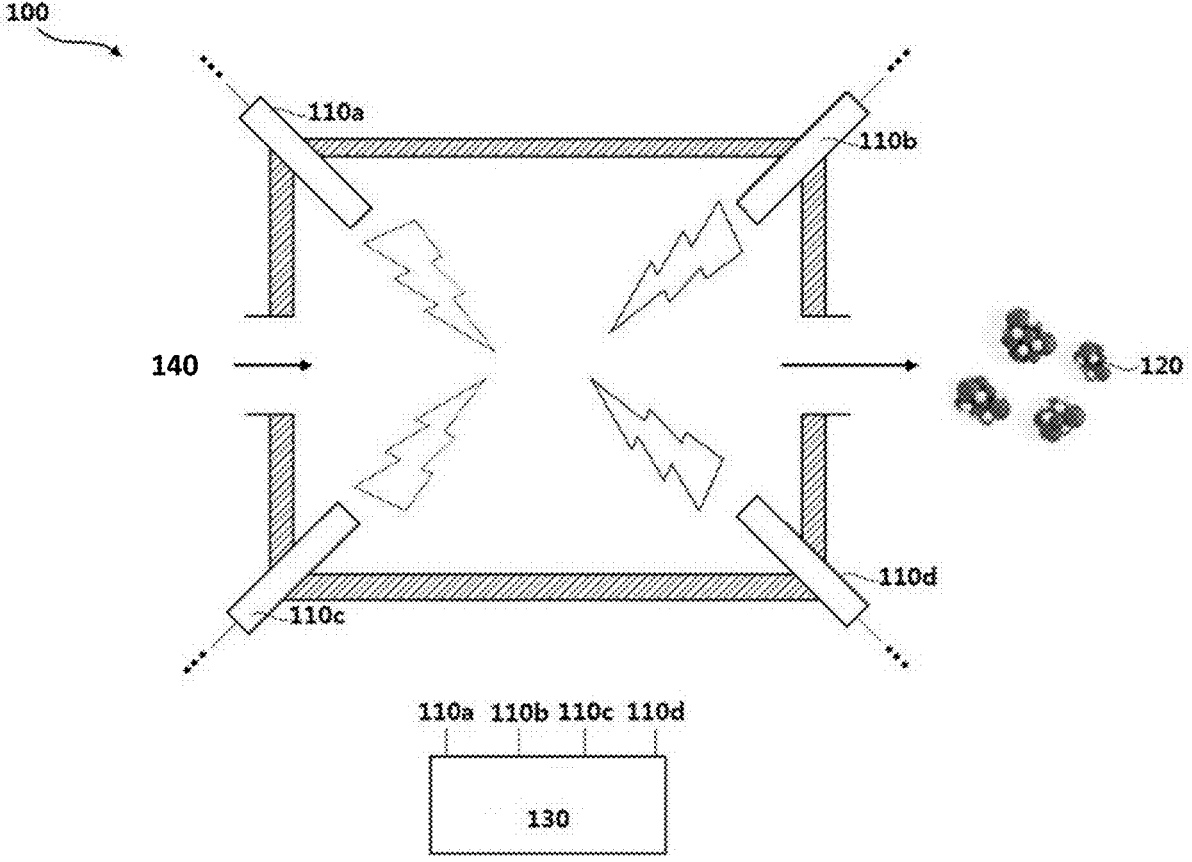
FIG. 3 is a diagram schematically illustrating a chamber in which nanoparticles (101) are formed.

FIG. 3 is a diagram schematically illustrating a chamber 100 in which the nanoparticles 120 are formed. Referring to FIGS. 1 to 3, the chamber 100 includes an inlet through which a carrier gas 140 is introduced and an outlet through which the carrier gas 140 is discharged. The chamber 100 includes a plurality of rods 110a, 110b, 110c, and 110d. For example, one or more of the rods may be a tellurium rod, and another one or more of the rods may be a silver rod. As an example, the carrier gas 140 may be nitrogen gas, and as another example, the carrier gas may be any one or more of air, argon, and a mixed gas thereof. In the illustrated embodiment, a configuration in which four rods are located in the chamber is described, but this is for illustration only, and less than four or five or more rods may be located in the chamber.

The plurality of rods 110a, 110b, 110c, and 110d may be connected to a voltage supply unit 130. The voltage supply unit 130 may provide a voltage so that the plurality of rods 110a, 110b, 110c, and 110d in the chamber 100 generate a spark discharge. In one embodiment, the voltage supplied from the voltage supply unit 130 may be in the range of 1,000 V to 10,000 V.

The spark discharge is accomplished in the chamber 100 by the plurality of rods 110a, 110b, 110c, and 110d. For example, as the spark discharge occurs in the tellurium rod, tellurium nanoparticles are formed in the chamber 100, and as the spark discharge occurs in the silver rod, silver nanoparticles are formed in the chamber 100, and the tellurium nanoparticles are doped with the silver nanoparticles to form the partially alloyed silver-telluride nanoparticles 120 (S100). The silver-telluride nanoparticles 120 are discharged to the outside of the chamber 100 through the outlet by the carrier gas. Antimicrobial activity of the silver-telluride nanoparticles 120 is similar to that of the silver nanoparticles, but cytotoxicity of the silver-telluride nanoparticles 120 is significantly lower than that of the silver nanoparticles, and thus no toxic substances are formed.

In another embodiment, the plurality of rods may be a copper (Cu) rod or a tellurium (Te) rod, and as the spark discharge occurs in the chamber, copper-telluride nanoparticles may be formed.

Figure 4A:
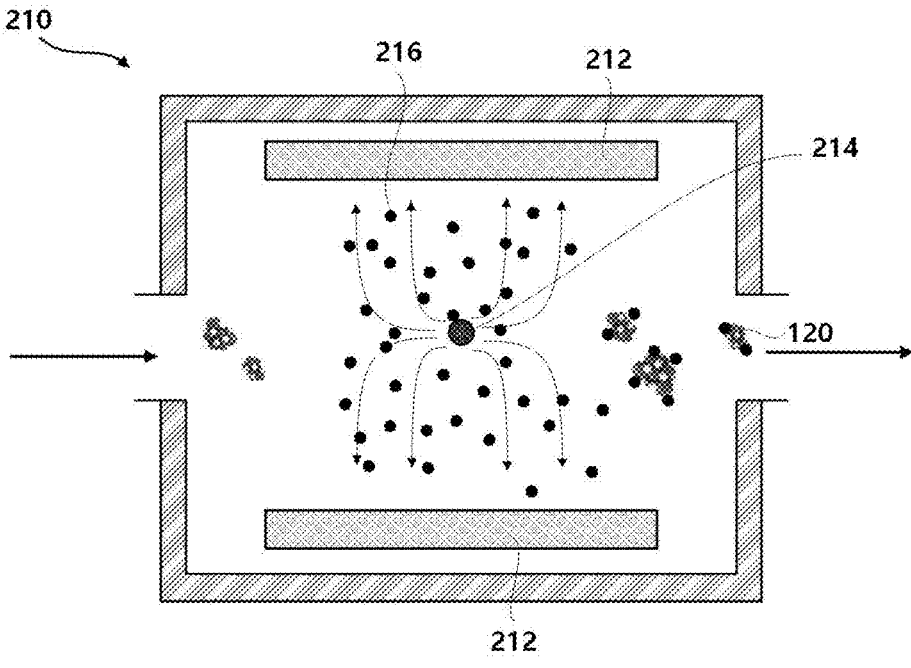
FIG. 4A is a diagram illustrating an example of a first charging chamber.
Figure 4B:
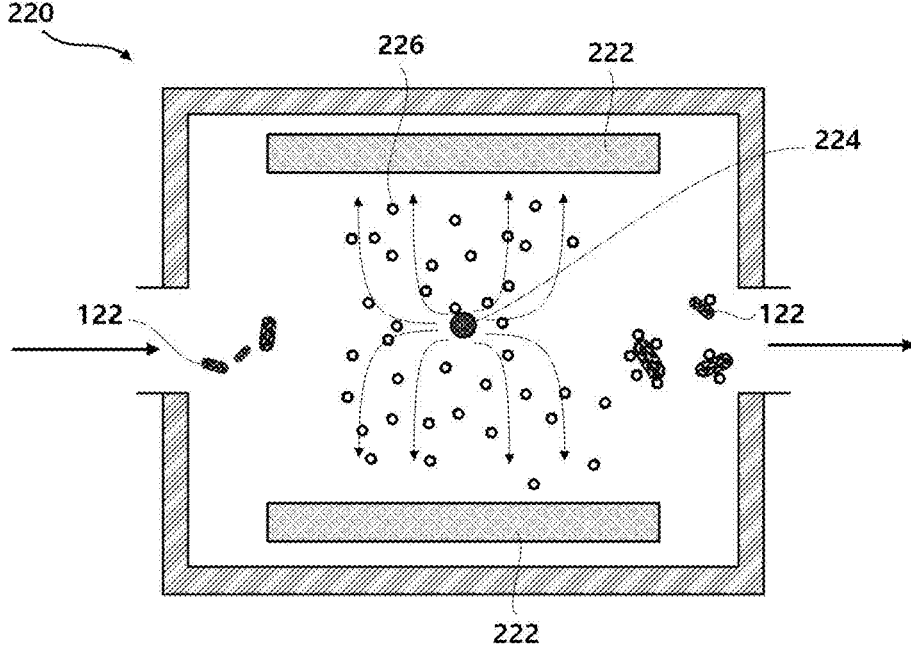
FIG. 4B is a diagram illustrating an example of a second charging chamber.

FIG. 4A is a diagram illustrating an example of a first charging chamber 210, and FIG. 4B is a diagram illustrating an example of a second charging chamber 220. Referring to FIG. 4A, the first charging chamber 210 includes a first wire 214 and a ground electrode 212, and the first wire 214 and the ground electrode 212 are discharged in the first charging chamber 210 to form ions 216 having a first polarity. The ions 216 having the first polarity are formed in the first charging chamber 210 and attached to the nanoparticles 120 to charge the nanoparticles 120 with the first polarity. A voltage may be supplied from the voltage supply unit 130 (see FIG. 3) to the first wire 214 so that the first wire 214 performs discharge.

In the example illustrated in FIG. 4A, the first polarity may be a negative polarity, and anions may be attached to the nanoparticles so that the nanoparticles are charged. For example, the anions may be anions such as $NO_3^- \cdot$ $C_3H_3O_3^- \cdot$ or $HSO_4^- \cdot$ As another example not illustrated, the first polarity may be a positive polarity, and cations may be attached to the nanoparticles so that the nanoparticles are charged. For example, the cations may be cations such as $H_3O^+ \cdot$ $H_2OH_3O^+ \cdot$ or $C_5H_{10}NO^+$. The anions and cations formed in the first charging chamber 210 and the second charging chamber 220 may appear differently depending on a discharge environment in the charging chamber.

Referring to FIG. 4B, the second charging chamber 220 includes a second wire 224 and a ground electrode 222, and the second wire 224 and the ground electrode 222 are discharged in the second charging chamber 220 to form ions 226 having a second polarity. The ions 226 having the second polarity are formed in the second charging chamber 220 and attached to the pathogens 122 to charge the pathogens 122 with the second polarity. A voltage may be supplied from the voltage supply unit 130 (see FIG. 3) to the second wire 224 so that the second wire 224 performs discharge.

In the example illustrated in FIG. 4B, the second polarity may be a positive polarity which is a polarity opposite to the polarity with which the nanoparticles are charged, and cations may be attached to the pathogens 122 so that the pathogens 122 are charged. As another example not illustrated, the second polarity may be a negative polarity which is a polarity opposite to the polarity with which the nanoparticles are charged, and anions may be attached to the pathogens 122 so that the pathogens 122 are charged.

Charge numbers $n_f$ of the nanoparticles 120 and pathogens 122 charged in the first charging chamber 210 and the second charging chamber 220 may be calculated as illustrated in the following Equation.

$$n_f = \left( \frac{3\varepsilon}{\varepsilon + 2} \right) \left( \frac{Ed_p^2}{4K_E e} \right) \left( \frac{\pi K_E e Z_i N_i t}{1 + \pi K_E e Z_i N_i t} \right) \quad \langle \text{Equation 1} \rangle$$

Here, $\varepsilon$ is relative permittivity, $d_p$ is a particle diameter, $Z_i$ is mobility depending on ion concentration, and $N_i$ is ion concentration.

The charged nanoparticles 120 and charged pathogens 122 each formed in the first charging chamber 210 and the second charging chamber 220 are discharged to the outlet. As an example, the charged nanoparticles 120 and charged pathogens 122 may be discharged by the carrier gas 140. As another example, the charged nanoparticles 120 and charged pathogens 122 may flow using an air pump (not illustrated) which is connected to the outlet of the first charging chamber 210 and the outlet of the second charging chamber 220 to suction and discharge the nanoparticles 120 and the charged pathogens 122. For example, the carrier gas 140 may be introduced through an inlet of the first charging chamber 210, and air 150 may be introduced through an inlet of the second charging chamber 220.

Figure 5:
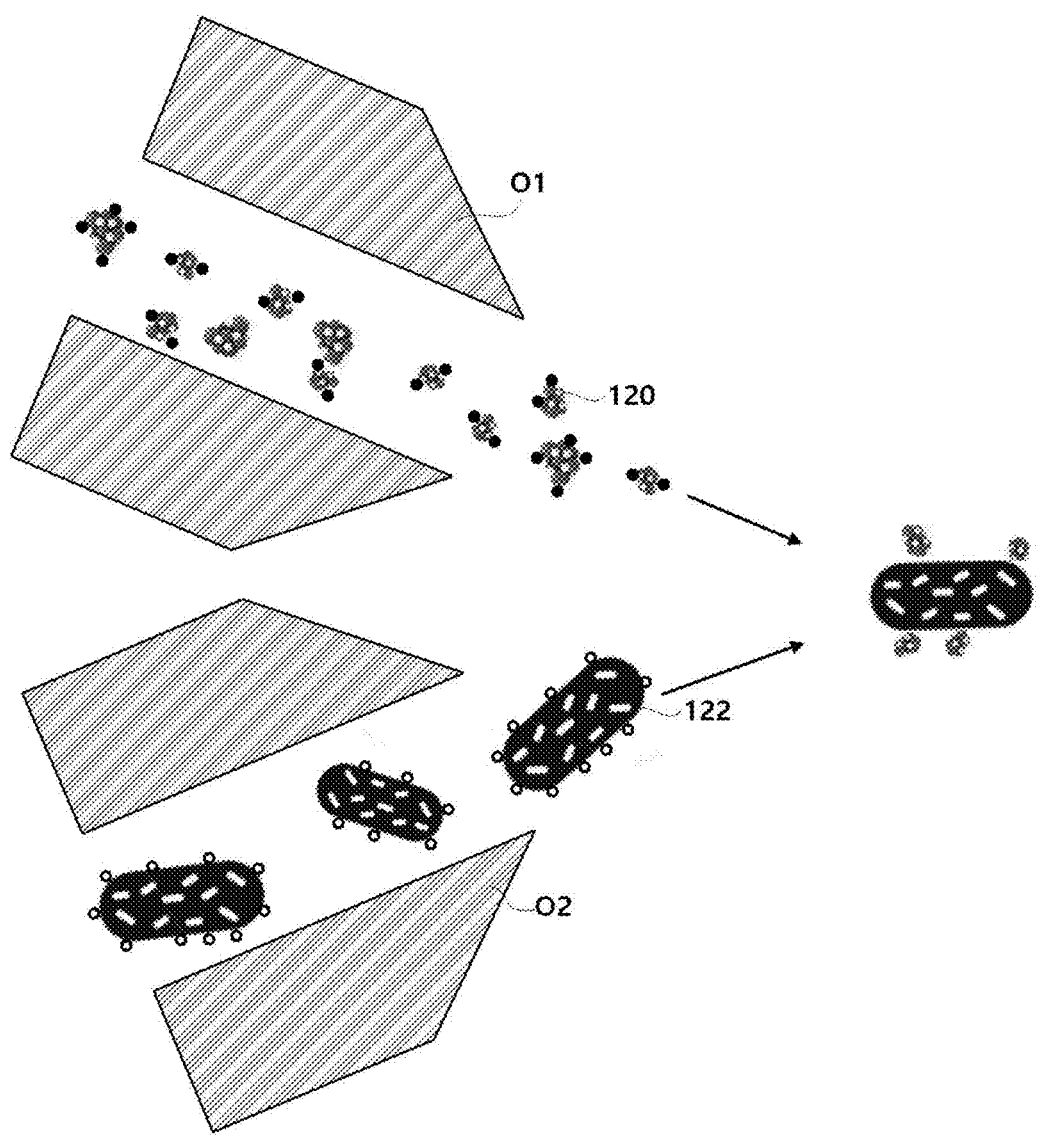
FIG. 5 is a diagram illustrating a step of extracting ATP by causing charged nanoparticles to collide with charged pathogens (122)

FIG. 5 is a diagram illustrating a step of extracting ATP by causing the charged nanoparticles 120 to collide with the charged pathogen 122. Referring to FIGS. 1 to 5, when the charged nanoparticles 120 and the charged pathogens 122 are discharged to a target position through an orifice O1 connected to the first charging chamber 210 and an orifice O2 connected to the second charging chamber 220, the charged nanoparticles 120 collide with the charged pathogens 122 by electrostatic attraction. The pathogens 122 hit by the nanoparticles 120 release ATP (S200). In one embodiment, a diameter of each of the orifices O1 and O2 may be 500 μm.

Figures 6, 7:
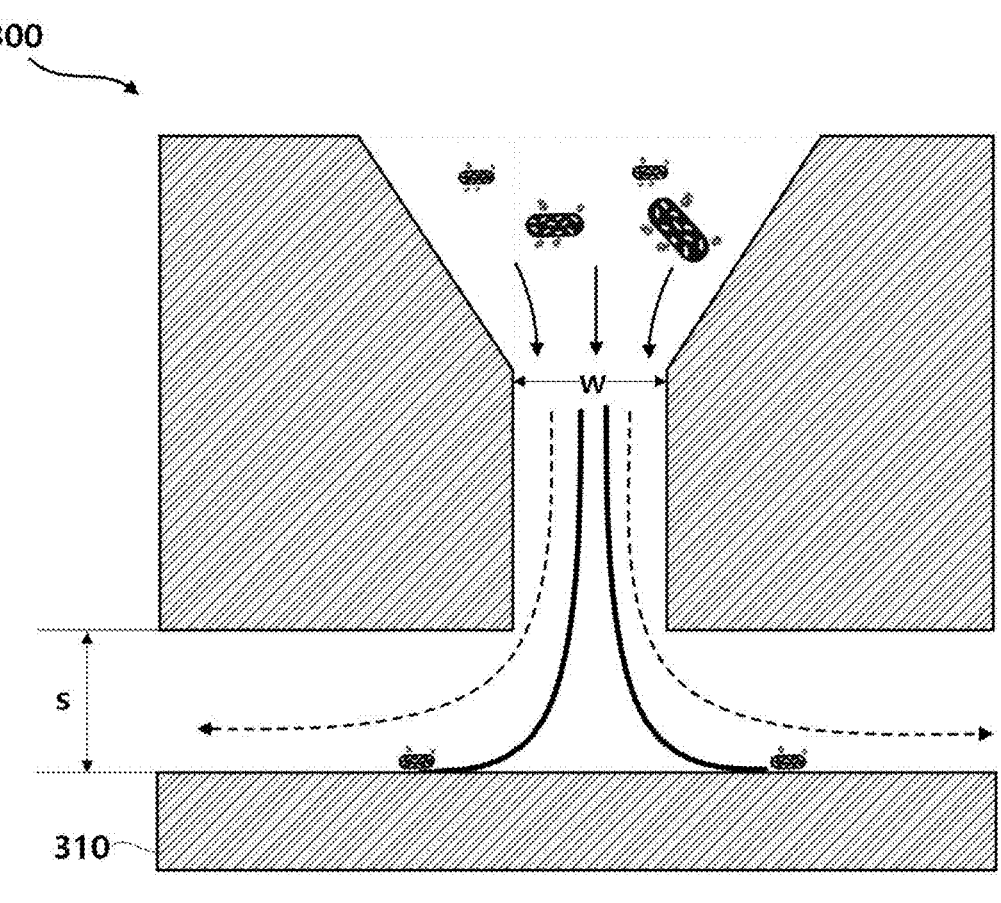
FIG. 6 is a diagram illustrating a particle impactor (300) and a streamline of particles introduced into the particle impactor (300)
FIG. 7 is a diagram schematically illustrating a step of detecting a light-emitting reaction.

FIG. 6 is a diagram illustrating a particle impactor 300 and a streamline of particles introduced into the particle impactor 300. Referring to FIG. 6, the particles introduced into the particle impactor 300 proceed in different paths depending on a flow velocity of gas and sizes of the particles. In FIG. 6, broken lines illustrate a streamline when light particles are introduced into the particle impactor, and the light particles proceed to the outlet without colliding with a collection plate 310 even when a flow direction of gas changes rapidly as illustrated.

However, when particles having a large size or a large mass such as the pathogens 122 having collided with the nanoparticles 120 are introduced into the particle impactor 300, the particles proceeds to the outlet at a portion where the flow direction of the gas changes, deviate from a streamline, collide with the collection plate 310, and are collected on the collection plate 310 (S300). In one embodiment, the size of bacteria floating in air is in the range of approximately 0.5 μm to 3 μm. Accordingly, when a flow rate, a diameter w of the inlet, and a diameter s of the outlet are set by setting a diameter of a separated particle to 0.5 μm, the impactor 300 can selectively collect the pathogens 122 having collided with the nanoparticles 120.

A geometric shape and operation variables of the impactor 300 are determined so that the impactor 300 can accurately separate particles of a desired size. A relationship between the particle diameter and the variables is expressed as the following Equation.

$$d_{50} = \sqrt{\frac{9\pi n \eta W^3 Stk_{50}}{4 C_c \rho_p Q}} \qquad \text{(Equation 2)}$$

Here, $d_{50}$ is a particle diameter when collection efficiency is 50%, n is the number of nozzles, $\eta$ is a viscosity coefficient of air, W is a nozzle diameter, $Stk_{50}$ is a Stokes number at the time of a separation particle diameter, $C_c$ is a slip correction factor, $\rho_p$ is a particle density, and Q is a suction flow rate.

The Stokes number is a ratio of a particle stopping distance to a nozzle radius and is expressed as Equation 3.

$$Stk = \frac{\rho_p d_p^2 U C_c}{9 \eta W} \qquad \text{(Equation 3)}$$

Here, U is an average speed at the nozzle.

In Equations 1 and 2, the nozzle radius means a radius of the gas passing through the nozzle, and the particle stopping distance can be obtained using an average exit velocity at the nozzle.

FIG. 7 is a diagram schematically illustrating a step of detecting the light emission reaction. Referring to FIGS. 1 to 7, the light emission reaction formed by reacting with the ATP emitted by the pathogens 122 is detected in a state in which the pathogens 122 are collected (S400). In one embodiment, materials 410 that react with ATP and cause the light emission reaction are sprayed onto an upper portion of the collection plate 310. For example, catalysts 420 that promote the light emission reaction may be further sprayed. For example, the material which causes the light-emitting reaction may be a material that emits light by reacting with ATP and may be luciferin, and the catalyst which promotes the light-emitting reaction may be luciferase. A sensor that detects the light-emitting reaction may be a light-receiving element 400 including a photodiode, and at least one light-receiving element 400 may be positioned above the collection plate 310 to detect a light emission phenomenon generated by the ATP emitted by the pathogens 122 and a substance causing the light-emitting reaction.

According to the present embodiment, since the collection of the pathogens and the reaction and detection with reaction reagents are performed on the collection plate 310, it is possible to quickly and easily perform the detection, the reagent for detecting the light emission is evaporated by air provided to the impactor 300, a method of periodically replacing or cleaning the collection plate 310 can be adopted, and thus high sensitivity can be maintained.

EXPERIMENTAL EXAMPLE

Figures 8A, 8B:
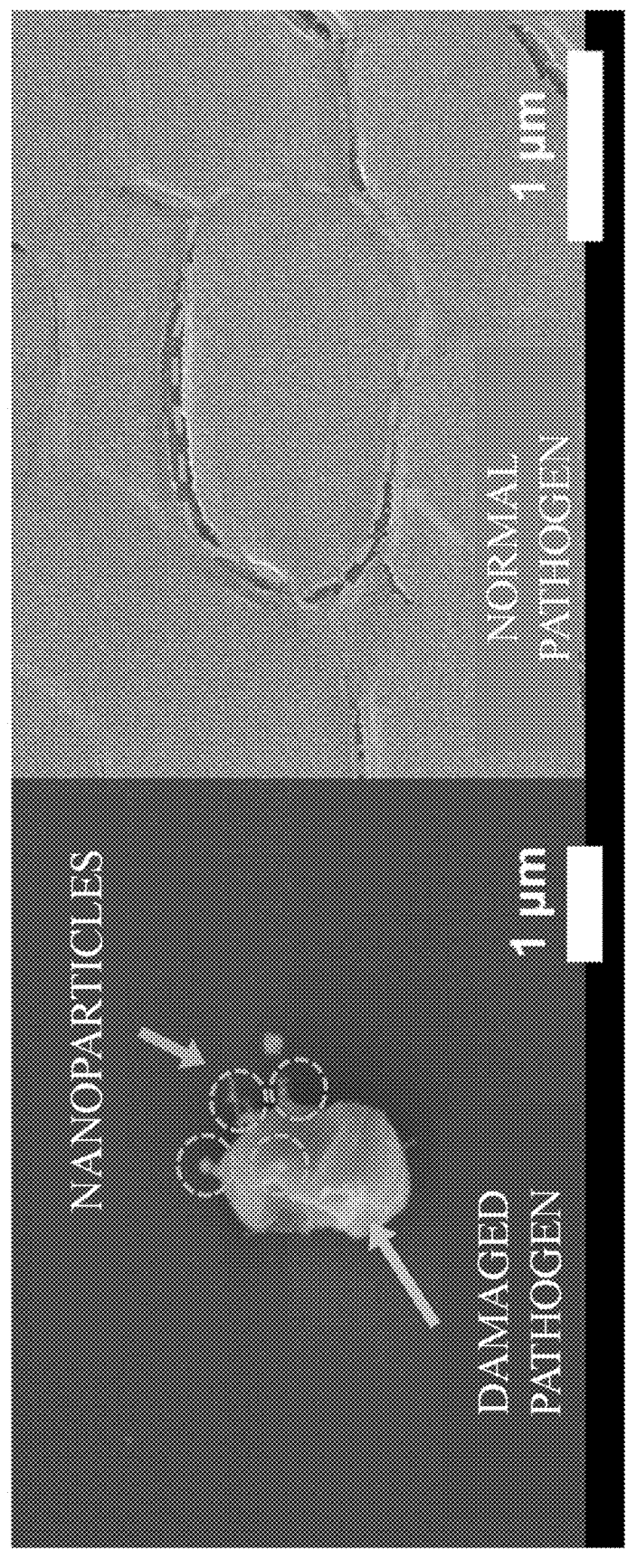
FIG. 8A is a micrograph illustrating a normal *Escherichia coli* bacteria pathogen and FIG. 8B is a micrograph illustrating a pathogen damaged by the impact of silver-doped tellurium nanoparticles.

Hereinafter, an experimental example of the present embodiment will be described with reference to FIG. 8. FIG. 8A is a micrograph illustrating a normal *Escherichia coli* bacteria pathogen, and FIG. 8B is a micrograph illustrating pathogens damaged by the impact of silver-doped tellurium nanoparticles. Referring to FIGS. 8A and 8B, the cell walls of the *Escherichia coli* bacteria, which are pathogens, contain a large amount of electrically negative polymers. It can be seen that the cell walls were damaged by adsorbing the sliver-doped tellurium nanoparticles having attached cations to the cell walls of the bacteria to which anions were attached.

According to present embodiment, the nanoparticles collide with aerosol-like pathogens to destroy the cell wall to extract the ATP, and thus it is possible to perform measurement quickly without the use of special reagents (PPDK), and there is an advantage that manual labor of the measurer is not required.

The present invention is described with reference to the embodiment illustrated in the drawings for understanding of the present invention. However, the embodiment is an embodiment for implementation and is only illustrative, and thus those of ordinary skill in the art will understand that various modifications and equivalent other embodiments are possible therefrom. Therefore, a true technical scope of the present invention should be determined by appended claims.

What is claimed is:

1. A pathogen detection apparatus comprising:
    a nanoparticle forming chamber in which nanoparticles are formed;
    an impact unit that causes the nanoparticles formed in the nanoparticle forming chamber to collide with pathogens so that adenosine triphosphate (ATP) is extracted from the pathogens, wherein the impact unit includes:
        a first charging chamber that charges the nanoparticles with a first polarity;
        a second charging chamber that charges the pathogens with a second polarity opposite to the first polarity;
        a nanoparticle orifice through which the nanoparticles charged with the first polarity in the first charging chamber are discharged to an impact point within the impact unit; and
        a pathogen orifice through which the pathogens charged with the second polarity in the second charging chamber are discharged to the impact point; and
    a detector including a collector and a sensor, wherein the collector comprises a collection plate to collect the pathogens having collided with the nanoparticles and the sensor comprises a light-receiving element to detect a light-emitting reaction formed by a reaction with the ATP emitted by the pathogens collected by the collector, and
    wherein the nanoparticles physically impact the pathogens so that the ATP from the pathogens is extracted.

2. The pathogen detection apparatus of claim 1, wherein the nanoparticle forming chamber forms tellurium particles doped with silver nanoparticles.

3. The pathogen detection apparatus of claim 2, wherein the nanoparticle forming chamber includes one or more tellurium rods and one or more silver rods, and
    wherein the pathogen detection apparatus further comprises a voltage supply unit that is connected to the one or more tellurium rods and the one or more silver rods, wherein the voltage supply unit provides a voltage to the one or more tellurium rods and the one or more silver rods to generate spark discharge in the one or more tellurium rods and the one or more silver rods and form the tellurium particles doped silver nanoparticles in the nanoparticle forming chamber.

4. The pathogen detection apparatus of claim 1, wherein the collector further comprises a particle impactor and the collector introduces the pathogens to which the nanoparticles are attached into the particle impactor to selectively collect the pathogens, to which the nanoparticles are attached, on the collection plate.

5. The pathogen detection apparatus of claim 1, wherein a luminescent material that reacts with the ATP to cause a light-emitting reaction and a catalyst to promote the light-emitting reaction are sprayed onto an upper portion of the collection plate.

6. The pathogen detection apparatus of claim 5, wherein the luminescent material is luciferin, and the catalyst is luciferase.

\*   \*   \*   \*   \*